(12) United States Patent
Anhorn et al.

(10) Patent No.: US 12,343,266 B2
(45) Date of Patent: Jul. 1, 2025

(54) SURGICAL INSTRUMENT (71) Applicant: Aesculap AG, Tuttlingen (DE)

(72) Inventors: Svenja Anhorn, Heroldstatt (DE); Franz-Peter Firmbach, Emmingen-Liptingen (DE)

(73) Assignee: Aesculap AG, Tuttlingen (DE)

( * ) Notice: Subject to any disclaimer, the term of this patent is extended or adjusted under 35 U.S.C. 154(b) by 280 days.

(21) Appl. No.: 18/321,998

(22) Filed: May 23, 2023

(65) Prior Publication Data

US 2023/0380990 A1    Nov. 30, 2023

(30) Foreign Application Priority Data

May 24, 2022   (DE) ..................... 10 2022 205 172.6

(51) Int. Cl.
*A61F 2/46*       (2006.01)
*A61B 17/02*     (2006.01)
*A61B 17/68*     (2006.01)

(52) U.S. Cl.
CPC ............ *A61F 2/461* (2013.01); *A61B 17/025* (2013.01); *A61B 2017/0268* (2013.01); *A61B 2017/681* (2013.01)

(58) Field of Classification Search
CPC ............................. A61F 2/461; A61B 17/155
See application file for complete search history.

(56) References Cited

U.S. PATENT DOCUMENTS

| 10,159,494 | B1 * | 12/2018 | Sah ...................... A61B 17/157 |
| 2012/0078263 | A1 * | 3/2012 | Parisi .................... A61F 2/3859 |
| | | | 623/20.14 |
| 2015/0045801 | A1 | 2/2015 | Axelson, Jr. et al. |
| 2017/0100132 | A1 | 4/2017 | Collazo |
| 2017/0290597 | A1 * | 10/2017 | Goble ................ A61B 17/1717 |
| 2021/0236143 | A1 * | 8/2021 | Shah ..................... A61F 2/3859 |
| 2022/0395281 | A1 * | 12/2022 | Nguyen ............... A61B 17/157 |
| 2023/0285032 | A1 | 9/2023 | Firmbach et al. |

FOREIGN PATENT DOCUMENTS

EP         4245229 A1      9/2023

* cited by examiner

*Primary Examiner* — Christian A Sevilla
(74) *Attorney, Agent, or Firm* — Christopher A. Rothe; CM Law (57) ABSTRACT

A surgical instrument for use in a knee joint replacement operation includes a reference block with a block rear face configured to bear on a resected femur, a stylus arranged on the reference block, a stylus tip configured to bear on the femur, and two reference feet that are spaced apart mediolaterally from one another and arranged on the reference block. Each reference foot has a foot upper face protruding beyond the block rear face. The foot upper faces are arranged in a common reference plane and are configured to bear on the femur. At least two reference bores extend from the block rear face. Each reference bore is configured to receive a reference pin. A compensation element is configured for form-fitting and/or force-fitting releasable connection to one of the reference feet. The compensation element has an upper face which comes to bear against a posterior condyle.

10 Claims, 6 Drawing Sheets

SURGICAL INSTRUMENT

CROSS-REFERENCE TO RELATED APPLICATIONS

This application claims priority under 35 U.S.C. § 119 to German Application No. 2022 205 172.6, filed May 24, 2022, the content of which is incorporated by reference herein in its entirety.

FIELD

The present disclosure relates to a surgical instrument for use in a knee joint replacement operation.

BACKGROUND

The use of orthopaedic prostheses as artificial replacements for damaged or worn natural bone structures is common medical practice. In particular, hip joint and knee joint replacement operations are nowadays routine in surgical orthopaedics.

In a knee joint replacement operation, or total knee arthroplasty (TKA), joint surfaces of the femur and/or tibia that have become worn or have been otherwise affected by disease or by injury are replaced by a knee joint prothesis. Such knee joint protheses usually comprise a femur component, which is implanted at the distal end of the femur, and a tibia component, which is implanted at the proximal end of the tibia. In order to ensure proper functioning of the artificial replacement joint, the aforementioned components have to be placed as precisely as possible in a defined position and orientation with respect to the anatomy of the patient and the axes of the patient's body. Otherwise, unsatisfactory results must be expected. There are different surgical approaches as regards the positioning of the components.

In an approach known as mechanical alignment, which has been the approach mainly used hitherto, the position and orientation of the artificial joint axes of the knee joint prosthesis have been provided so as to be mechanically ideal, without consideration being given to any orthopaedic deformities presented by the patient. The longitudinal axis of the tibia has often been used here as a reference axis for the orientation and positioning. Clinical studies have shown that the mechanical alignment approach can lead to the function of the artificial knee joint being felt unnatural.

A further approach is what is known as kinematic alignment (also shortened to KA below). In this technique, the femur component and the tibia component are positioned taking into consideration any orthopaedic deformities presented by the patient. The aim is to restore the patient's natural joint orientation, which in some cases is affected by deformity. Clinical studies have shown that the kinematic alignment approach is often associated with improved patient satisfaction. In particular, the function of the artificial knee joint is felt by the patient to be more natural.

With the aim of further improving patient satisfaction, there is a fundamental need for surgical instruments that are as precise as possible, easy to use and cost-effective for the implementation of kinematic alignment. The present disclosure deals with such a surgical instrument, specifically with a surgical instrument for determining a size and for setting an (internal/external rotation, I/E rotation for short) of the femur component. Such instruments are also referred to as a femoral sizer or femoral sizing system. Different femoral sizers are known from the prior art.

SUMMARY

It is the object of the present disclosure to make available a surgical instrument which affords advantages over the prior art and in particular permits improved setting of the I/E rotation and/or determination of size.

The surgical instrument according to the disclosure has: a reference block with a proximally oriented block rear face which is configured to bear on a distal end face of a resected femur, a stylus which is arranged on the reference block in the region of an anterior block upper face thereof and has a stylus tip which protrudes proximally beyond the block rear face and is configured to bear on an anterior face of the femur, two reference feet which are spaced apart mediolaterally from one another and are each arranged on the reference block in the region of an underside thereof lying posteriorly opposite the block upper face and each have an anteriorally oriented foot upper face protruding proximally beyond the block rear face, wherein the foot upper faces are arranged in a common reference plane and are each configured to bear on a posterior condyle of the femur, at least two reference bores which each extend orthogonally to the block rear face continuously from the latter as far as a distally opposite block front face and are each configured for receiving a reference pin which can be introduced into the distal end face of the femur, wherein the at least two reference bores are spaced apart from one another along a virtual spacing line which is elongate mediolaterally and parallel to the reference plane, wherein there is at least one compensation element which is configured for form-fitting and/or force-fitting releasable connection to one of the two reference feet, and wherein the at least one compensation element has an anteriorly oriented element upper face which comes to bear, instead of the relevant foot upper face, against the relevant posterior condyle.

The solution according to the present disclosure is based on the finding that the setting of the I/E rotation and/or the determination of size within the scope of KA should ideally take place starting from the original posterior condyle line of the femur. Originally in this context means without condyle defects, such as, for example, cartilage erosion, injury damage or the like. If condyle defects are present, the posterior condyle line consequently deviates from its original alignment. Setting the I/E rotation and/or determining the size on the basis of the defective, i.e. not original, posterior condyle line of the femur can lead to unsatisfactory results. The disclosure counteracts this. It is because defects at the posterior condyle can be taken into consideration by the solution according to the disclosure when setting the I/E rotation and/or determining the required size of the femur component. It has been shown that improved results can thereby be obtained.

For this purpose, the surgical instrument according to the disclosure has the at least one compensation element. The at least one compensation element can be selectively attached to one of the two reference feet, more precisely: to the foot upper faces thereof. In simplified terms, an anteroposterior dimension of the reference foot is changed as it were by the compensation element and said defect is thereby dimensionally compensated for. In the attached state of the compensation element, instead of the relevant foot upper face, the element upper face of the compensation element bears against the relevant (defective) posterior condyle. By this means, the defect is dimensionally compensated for and the original posterior condyle line restored. In the attached state, the at least one compensation element forms a form-fitting and/or force-fitting connection to the relevant reference foot.

The connection can be, for example, a plug-in, latching, clamping and/or snap-fit connection. The connection is formed releasably and directly between the at least one compensation element and the relevant reference foot, i.e. without the assistance of a separate connecting means. The reference block is used for distal referencing at the resected femur. For this purpose, the reference block has the proximally oriented block rear face. During use of the surgical instrument, said block rear face bears against the distal end face. The two reference feet are used for referencing at the posterior condyles of the femur. For this purpose, the two reference feet each have an anteriorally oriented foot upper face. If the at least one compensation element is not attached to any of the reference feet, the two foot upper faces bear against one of the two posterior condyles each.

In one embodiment, the two reference feet are each arranged fixedly on the reference block and/or are designed as a section of same. In a further embodiment the reference feet are each connected releasably as a separate component to the reference block. The reference feet are spaced apart from one another mediolaterally and can also be referred to as a lateral reference foot and medial reference foot. The lateral reference foot is configured here for bearing against the lateral posterior condyle. The medial reference foot is accordingly configured to bear against the medial posterior condyle. The stylus is used for the actual determination of the size of the femur and therefore the required size of the femur component to be implanted. For this purpose, the stylus has the stylus tip. After distal referencing has taken place by means of the block rear face and posterior referencing by means of the foot upper faces (and optionally the at least one compensation element), the stylus tip is brought into contact with the anterior face of the femur. For this purpose, the stylus tip is preferably proximodistally and/or anteroposteriorally relatively movable. The required size can be read, for example, using a scale assigned to the stylus.

In one embodiment, the stylus is fixedly connected to the reference block. In a further embodiment, the stylus is attached removably to the reference block. The reference bores are used for receiving said reference pins. After alignment has taken place, said reference pins are introduced from the block front face through the reference bores into the distal end face of the resected femur. The surgical instrument can then be pulled off distally from the reference pins. The reference pins remain in the femur and serve for subsequent fastening of what is referred to as a femoral cutting jig. Consequently, the positioning of the reference bores predetermines the later alignment of the femoral cutting jig and therefore also the alignment of the cuts to be made on the femur by it. The alignment of the cuts ultimately determines the UE rotation of the femoral component. In one embodiment, the reference bores are introduced directly into the reference block. In a further embodiment, the reference bores are formed on a separate component which is connectable, preferably releasably, to the reference block.

The position and direction designations used in this description relate to the body of a patient, in particular the femur of the patient, and to this extent they are to be understood in accordance with their usual anatomical meaning. Consequently, "anterior" denotes front or lying to the front, "posterior" denotes rear or lying to the rear, "medial" denotes inner or lying to the inside, "lateral" denotes outer or lying to the outside, "proximal" denotes towards the centre of the body, and "distal" denotes away from the centre of the body. Furthermore, "proximodistal" denotes along, preferably parallel to, a proximal-distal axis, "anteroposterior" denotes along, preferably parallel to, an anterior-posterior axis, and "mediolateral" denotes along, preferably parallel to, a medio-lateral axis. The aforementioned axes are orthogonal to one another and can of course be understood in relation to X, Y and Z axes not associated with the anatomy of the patient.

For example, the proximal-distal axis can be designated alternatively as the X axis. The medial-lateral axis can be designated as the Y axis. The anterior-posterior axis can be designated as the Z axis. For the sake of better illustration and simplicity of the designations, the aforementioned anatomical position and direction designations are primarily used in the following. Moreover, designations such as the "rear face" of a component or of a portion of the surgical instrument, for example of the reference block, are used with respect to a proximally oriented viewing direction. By contrast, designations such as "front face" are used with respect to a distally oriented viewing direction.

In one embodiment of the disclosure, the at least one compensation element has, on its element underside, a receiving pocket which is sunk anteriorally and is open posteriorally and in which the reference foot can be received in a form-fitting manner. The receiving pocket permits a particularly simple and nevertheless reliable attachment of the compensation element to the relevant reference foot. The receiving pocket is sunk into the element underside, the element underside lying posteriorally opposite the element upper face. In other words, in the attached state of the compensation element, the element underside faces the relevant foot upper face. The receiving pocket is posteriorally open. By this means, the compensation element can be attached in the posterior direction to the reference foot. The receiving pocket forms a plug-in, latching and/or clamping connection to the reference foot. The receiving pocket is complementary to the reference foot, and vice versa. In other words, the receiving pocket forms a type of negative shape of the reference foot. In an alternative embodiment, the compensation element has a slit arranged anteroposteriorially between the element underside and the element upper face for distally plugging it onto the reference foot.

In a further embodiment of the disclosure, the at least one compensation element has, on its element underside, an outer rim which protrudes posteriorally and in particular surrounds the receiving pocket and is connectable in a form-fitting manner to an outer circumference of the reference foot. In the attached state, the outer rim engages around the outer circumference of the reference foot. By this means, a releasable plug-in, latching and/or clamping connection is formed between the at least one compensation element and the relevant reference foot. The outer rim engages at least in sections around the outer circumference of the reference foot. If the at least one compensation element has a receiving pocket according to the previous embodiment, the outer rim forms the boundary thereof.

In a further embodiment of the disclosure, the outer rim is elastically flexible. The elastic flexibility can be brought about by material and/or design. For example, the outer rim, preferably the entire at least one compensation element, can be manufactured from an elastically flexible material, for example a plastic, in particular an elastomer. Alternatively or additionally, the outer rim can be of thin-walled dimensions. The thin-walled dimensioning can bring about or at least assist the aforementioned elastic flexibility. In the attached state of the compensation element, the elastic flexibility brings about an elastic prestress on the outer circumference of the reference foot. This counteracts an inadvertent release of the compensation element.

In a further embodiment of the disclosure, the at least one compensation element has a lateral element section, a medial element section, a separating gap, which separates the two element sections from one another and is elongate proximodistally and is open at one end, and a joint section which is arranged at the other end of the separating gap and connects the two element sections to one another in an elastically movable-joint manner. This embodiment permits a further improvement in the connection between the compensation element and the relevant reference foot. As a result of the separating gap and the joint section, the two element sections are elastically movable relative to one another. Such elastic movability is particularly advantageous in combination with the receiving pocket and/or the outer rim according to the preceding embodiments. When the compensation element is plugged, latched or clamped to the reference foot, the two element sections spring apart transversely with respect to the longitudinal extent of the separating gap. The elastic restoring force causes additional contact forces between the compensation element and the reference foot. The additional contact forces are associated with increased friction. The increased friction counteracts an unintentional release of the compensation element from the relevant reference foot. The lateral element section, the medial element section and the joint section are integral. The joint section may also be referred to as a solid body joint.

In a further embodiment of the disclosure, there are a plurality of different compensation elements, the different compensation elements differing, preferably exclusively, in respect of a respective anteroposterior thickness. Condyle defects varying greatly in extent can be compensated for with the aid of the different compensation elements. The differing extent of the defects is taken into account by the different thicknesses of the compensation elements. A defect which is weak in relation can be compensated for with a comparatively less thick compensation element. Conversely, a defect which is strong in relation can be compensated for by a comparatively thick compensation element. Apart from their different thicknesses, the different compensation elements are preferably identical. In one embodiment, the two reference feet are identical in terms of their dimensions and/or shape. In this case, each of the different compensation elements can be selectively attached to the two reference feet. In a further embodiment, the two reference feet have a different shape and/or different dimensions. In this case, a separate set of different compensation elements can be assigned to each of the two reference feet.

In a further embodiment of the disclosure, there are at least three different compensation elements having a respective thickness of 1 mm, 2 mm and 3 mm. The inventors have identified that a value range from 1 mm to 3 mm and a corresponding graduation by 1 mm in each case are particularly advantageous. This is because, firstly, said value range permits the compensation of significantly greatly varying defects. Secondly, said graduation makes it possible to keep the number of different compensation elements small. Compared to a fundamentally conceivable more precise graduation in steps of, for example, 0.5 mm.

In a further embodiment of the disclosure, the reference block has an aperture reaching between the block rear face and the block front face, and an alignment element which is arranged in the aperture, is elongate substantially anteroposteriorally and is configured for alignment along the Whiteside's line of the femur. This embodiment permits a further improvement in the setting of the I/E rotation. The aperture can also be designated an opening or viewing opening. During the use of the surgical instrument, the aperture permits visual checking of the distal femur by the operating surgeon. In other words, the surgeon starting from the block front face can look through the aperture at the distal end face of the resected femur, said distal end face bearing against the block rear face. The alignment element is arranged in the aperture and is elongate substantially anteroposteriorally. The I/E rotation is set by the reference block being aligned together with the alignment element relative to the aforementioned Whiteside's line. The Whiteside's line denotes the anteroposterior axis of the distal femur and can also be referred to as the trochlea axis. The Whiteside's line is aligned orthogonally with respect to what is referred to as the transepicondyle axis of the distal femur. The posterior condyle line should be differentiated therefrom. The alignment element is oriented differently in different embodiments with respect to the common reference plane of the foot upper faces—and therefore also with respect to the virtual spacing line between the reference bores. In one embodiment, there is an orthogonal orientation. This corresponds to a (neutral) YE rotation of 0°. In one embodiment, there is a deviation of 3° from the orthogonal, and 5° in a further embodiment. This corresponds to an YE rotation of 3° or 5°. An internal or an external rotation can be set depending on the sign. In a further embodiment, the orientation of the alignment element can be changed, preferably in a graduated manner, with respect to the common reference plane and/or virtual spacing line.

In a further embodiment of the disclosure, the alignment element is movable relative to the reference block between a first position, in which the alignment element is oriented at a first angle with respect to the virtual spacing line of the reference bores, and a second position, in which the alignment element is oriented at a second angle with respect to the virtual spacing line of the reference bores. By shifting the alignment element between the first position and the second position, the YE rotation can be accordingly selectively set. Alternatively, it is conceivable for the first angle and the second angle to be identical in value and to be denoted by different signs. By this means, the surgical instrument can be used in the first position of the alignment element for the left knee and in the second position for the right knee and in each case an YE rotation identical in terms of value can be set.

In a further embodiment of the disclosure, the alignment element has a posterior end, which is mounted on the reference block so as to be movable about a proximodistally oriented pivot axis, and an anterior end, which protrudes beyond the block upper face and is configured for manual movement of the alignment element between the first position and the second position. This embodiment permits a particularly reliable and ergonomic setting of the alignment element and therefore of the UE rotation. For this purpose, the alignment element is mounted at one end, at its posterior end, on the reference block. More precisely, the alignment element is mounted on the reference block so as to be pivotable about the proximodistally oriented pivot axis. In one embodiment, the pivot axis is an imaginary geometrical axis. In a further embodiment, the pivot axis is defined by means of a physically present component, i.e., an axle. The pivot axis is oriented orthogonally with respect to the block rear face. The anterior end of the alignment element facing away from the pivot axis is used for the manual movement.

To be able to reach it better manually, the anterior end protrudes beyond the block upper face.

BRIEF DESCRIPTION OF THE DRAWING FIGURES

Further advantages and features of the disclosure will become clear from the following description of a preferred exemplary embodiment of the disclosure, which is illustrated with reference to the drawings.

DETAILED DESCRIPTION

According to FIGS. 1 to 4, a surgical instrument 1 is provided for use in a knee joint replacement operation and has a reference block 100, a stylus 200, two reference feet 300, 400, two reference bores 107, 108 and at least one compensation element 500.

The reference block 100 has a proximally oriented block rear face 101, a distally opposite block front face 102, an anterior block upper face 103, a posterior block underside 104, a lateral block outer face 105 and a medial block outer face 106. The block rear face 101 is configured to bear on a distal end face S of a resected femur F (see FIG. 4). A normal direction of the block rear face 101 is oriented parallel to the proximodistal axis indicated in FIGS. 1 and 2 and points in the proximal direction.

The stylus 200 is attached to the reference block 100 in the region of the anterior block upper face 103 and has a stylus tip 201. The stylus tip 201 protrudes proximally beyond the block rear face 101 and is configured to bear on an anterior face A of the femur (see FIG. 4). In the present embodiment, the stylus 200 is connected releasably to the reference block 100 in a manner to be described in detail. In an embodiment not illustrated graphically, the stylus is fixedly connected to the reference block.

The two reference feet 300, 400 are also referred to below as lateral reference foot 300 and medial reference foot 400. The two reference feet 300, 400 are spaced apart from one another along the mediolateral axis, indicated in FIGS. 1 and 2, and are in each case arranged in the region of the block underside 104 of the reference block 100. In the embodiment which is shown, the two reference feet 300, 400 are each arranged fixedly on the reference block 100. Specifically, the reference feet 300, 400 each form a section of the reference block 100. In an embodiment which is not illustrated in the figures, the reference feet are in each case a separate component which is connected releasably to the reference block. The two reference feet 300, 400 each have an anteriorally oriented foot upper face 301, 401 protruding proximally beyond the block rear face 101. The foot upper faces 301, 401 are also referred to below as lateral foot upper face 301 (of the lateral reference foot 300) and medial foot upper face 401 (of the medial reference foot 400). The two foot upper faces 301, 401 are arranged at the same height with respect to the anteroposterior axis and to this extent in a common plane. The aforementioned plane is referred to as the reference plane R (see FIG. 2). The foot upper faces 301, 401 are oriented orthogonally with respect to the block rear face 101 and are each configured to bear on a posterior condyle KM, KL (see FIGS. 4 and 5). The lateral foot upper face 301 is configured to bear on the lateral posterior condyle KL. The medial foot upper face 401 is configured to bear on the medial posterior condyle KM (see FIG. 5).

The two reference bores 107, 108 each extend orthogonally to the block rear face 101 reaching right between the block rear face 101 and the block front face 102. The reference bores 107, 108 are spaced apart from one another mediolaterally and are also referred to below as lateral reference bore 107 and medial reference bore 108. The reference bores 107, 108 are spaced apart from one another along a virtual spacing line L. The virtual, i.e. imaginary, spacing line L is elongate between bore centre points, not denoted specifically, of the reference bores 107, 108. The virtual spacing line L is elongate parallel to the foot upper faces 301, 401 and therefore also to the reference plane R. The reference bores 107, 108 are each configured for receiving a reference pin, not denoted specifically in the figures. The aforementioned reference pins can be introduced, for example, in the intraoperative situation shown with reference to FIG. 4, from the block front face 102 in the proximal direction through the respective reference bore 107, 108 into the distal end face S. After removal of the surgical instrument 1 from the femur F, the reference pins remain in situ and are used for fastening a femoral cutting jig. This will be discussed in more detail below. In the embodiment shown, the reference bores 107, 108 extend directly through the reference block 100 and/or are introduced into same. In an embodiment which is not shown in the figures, the reference bores are introduced into a separate component which is connected, preferably releasably, to the reference block.

In the configuration shown in FIGS. 1 to 4, the at least one compensation element 500 is attached to the medial reference foot 400. For this purpose, the compensation element 500 is configured for the force-fitting and/or form-fitting releasable connection to the medial reference foot 400. The aforementioned releasable connection is formed directly between the compensation element 500 and the medial reference foot 400, i.e. is produced without additional connecting means. This is done in a manner still to be described in detail. The compensation element 500 has an anteriorally oriented element upper face 501 (see in particular FIG. 3). The element upper face 501 is oriented plane-parallel to the reference plane R and therefore orthogonally to the block rear face 101. During the use of the surgical instrument 1, depending on whether the compensation element 500 is or is not attached to the medial reference foot 400, either the medial foot upper face 401 or instead the element upper face 501 comes to bear on the medial condyle KM.

The function of the surgical instrument 1 and in particular the purpose of the at least one compensation element 500 will be explained in detail below by way of example with reference to the intraoperative situation according to FIG. 4.

Figure 4:
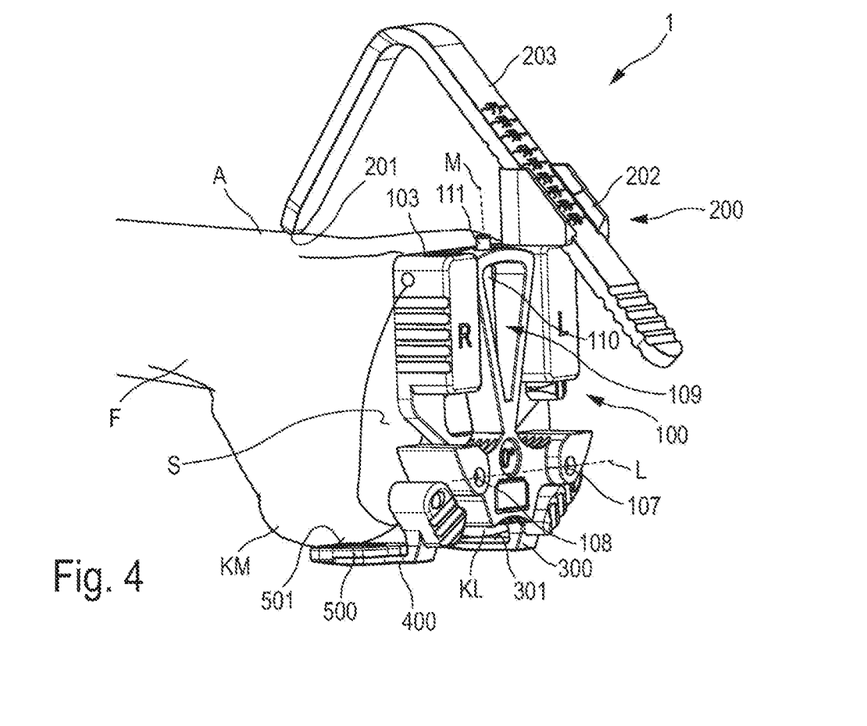
FIG. 4 shows a schematic perspective view of an exemplary intra-operative situation in which the surgical instrument is applied to a resected distal femur.

The surgical instrument 1 is used for multiple purposes. Firstly, a size measurement and/or check can be carried out at the distally resected femur F by means of the surgical instrument 1. Secondly, the surgical instrument 1 is used for setting of what is referred to as the I/E rotation. In detail:

After a distal femoral cut has been made, the surgical instrument 1 is placed against the resulting end face S (see FIG. 4). The block rear face 101 makes contact here with the end face S. The two reference feet 300, 400 engage under the posterior condyles KM, KL.

For the further explanation, two exemplary states are distinguished below.

Figure 5:
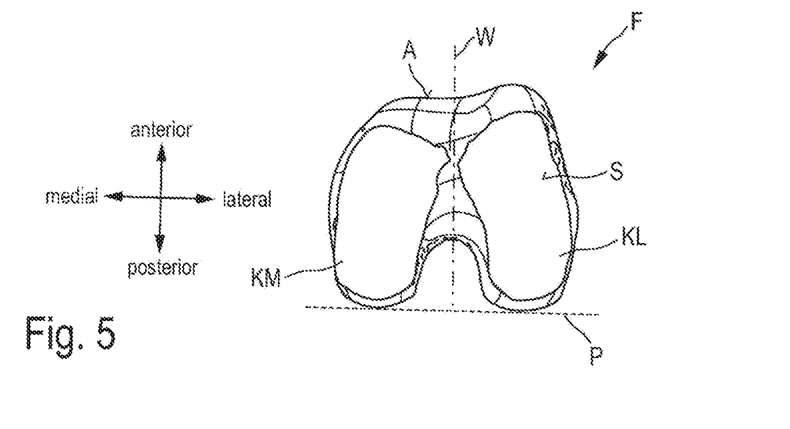
FIG. 5 shows the resected femur according to FIG. 4 in a proximally directed viewing direction and with the surgical instrument blanked out.

In a first state, the posterior condyles KM, KL do not have a defect, i.e. in particular do not have cartilage erosion and/or bone wear. In the first state, what is referred to as the posterior condyle line P runs as illustrated in FIG. 5. This state of the posterior condyle line P can also be referred to as "original", i.e. is not influenced by any condyle defects.

In a second state, the medial condyle KM has a defect which is not shown in detail in the figures. In the second state, the posterior condyle line in the region of the condyle KM deviates upwards with respect to the plane of the drawing from the original situation shown in FIG. 5. Expressed in other words, the posterior condyle line is rotated about a proximodistal axis in the second state.

In the first state, a posterior referencing can take place without the compensation element. In this case, the lateral foot upper face 301 is placed onto the lateral posterior condyle KL and the medial foot upper face 401 is placed onto the medial posterior condyle KM. In this case, the (original) posterior condyle line P extends in the reference plane R. The virtual spacing line L is elongate parallel thereto. After the aforementioned reference pins are placed through the reference bores 107, 108, the surgical instrument 1 is removed and the femoral cutting jig attached, the latter is aligned in a (neutral) I/E rotation of 0° with respect to the proximodistal axis. For the sake of simplicity, the starting point below is that such an alignment is desirable in particular within the scope of KA and is associated with particular surgical/medical advantages.

In the defective second state, such a (neutral) I/E rotation cannot be readily ensured. This is because the previously described deviation of the posterior condyle line from its original state naturally results in rotation of the virtual spacing line L and consequently also rotation of the femoral cutting jig. In order to counteract this, there is the at least one compensation element 500. To compensate for the aforementioned defect, the compensation element 500 is attached here to the medial posterior condyle KM. Instead of the medial foot upper face 401, the element upper face 501 now comes to bear against the medial posterior condyle KM. By this means, the defect is dimensionally compensated for and, as a result, the posterior referencing takes place as though the original posterior condyle line P were present as before.

Figure 6:
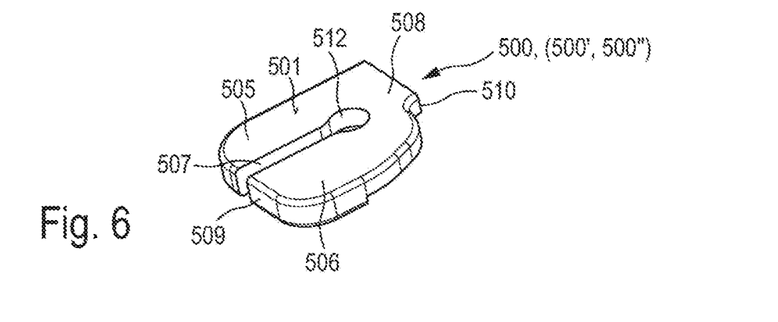
FIGS. 6, 7 and 8 show enlarged detailed illustrations of a compensation element of the surgical instrument in a schematic perspective view (FIG. 6), a schematic plan view (FIG. 7) and a schematic bottom view (FIG. 8)
Figure 7:
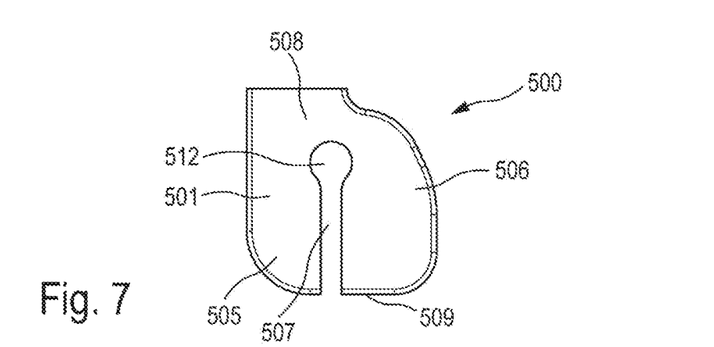
Figure 11:
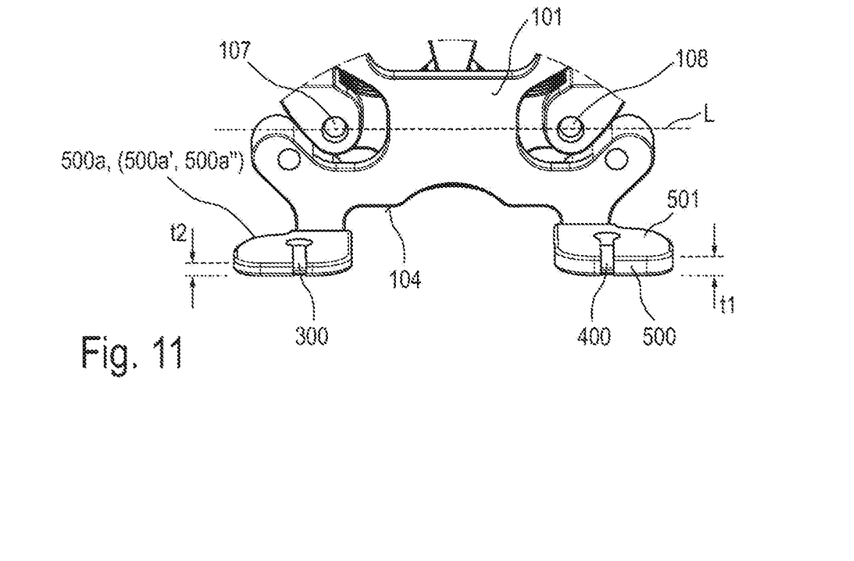
FIG. 11 shows a partial illustration of the surgical instrument in a configuration in which there are two different compensation elements.
Figure 12:
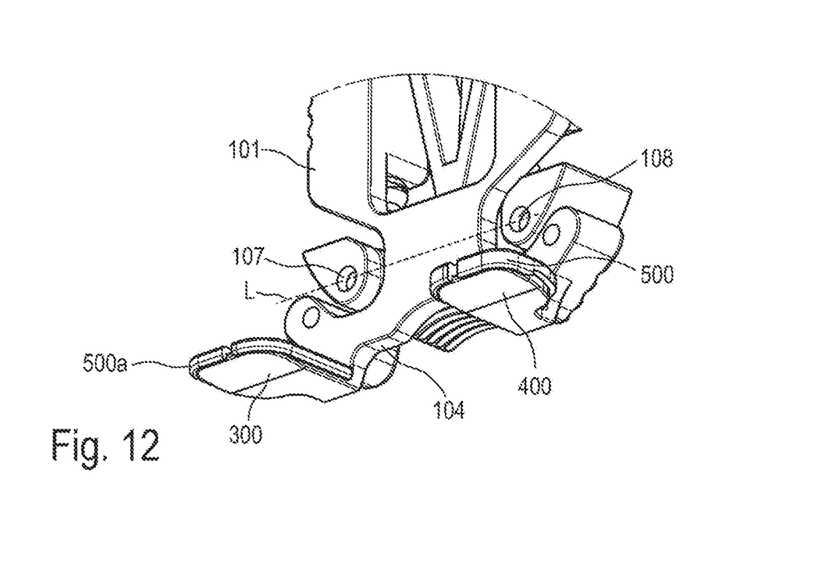
FIG. 12 shows the configuration according to FIG. 11 in a further schematic perspective view.

For the dimensional compensation of defects varying greatly in extent, the surgical instrument here has not only the compensation element 500 shown in FIGS. 1 to 4. Rather, there are a plurality of different compensation elements 500, 500', 500" having a different anteroposterior thickness. The further compensation elements 500', 500" are not illustrated separately in the figures and, apart from the different anteroposterior thickness, have an identical design and function to the compensation element 500. In addition, it goes without saying that compensation can take place not only in the region of the medial posterior condyle KM, but alternatively or additionally at the lateral posterior condyle KL. For this purpose, the surgical instrument 1 here has further compensation elements 500a, 500a', 500a" which can be attached to the lateral reference foot 300. A compensation element 500a of this type is shown in FIGS. 11 and 12. The presence of the further compensation elements 500', 500" and 500a', 500a" is clarified by the reference signs between parentheses in FIGS. 6 and 11. Furthermore, FIGS. 11 and 12 show an exemplary situation in which compensation elements of differing thickness are used. The compensation element 500 has a first thickness t1. The laterally attached compensation element 500a has a second thickness t2.

For the measuring and/or checking of the size of the femur F, the stylus tip 201 is brought to bear against the anterior surface A. The stylus tip 201 here is mounted so as to be movable relative thereto for this purpose. Specifically, the stylus 200 here has a stylus base 202 and a stylus rod 203 on which the stylus tip 201 is arranged at one end. The stylus rod 203 is guided slidably on the stylus base 202 along a guide axis, not denoted specifically. The stylus base 202 is attached releasably to the reference block 100. The further design and the function of the stylus specifically are not essential for the present disclosure. Therefore, further explanations in this regard are not necessary.

Further features of the compensation element 500 and the function thereof will be explained in detail below. That stated with regard to the compensation element 500 also applies, mutatis mutandis, to the further compensation elements 500', 500" and 500a, 500a' and 500a".

Different types of joining connections are conceivable in principle for the releasable attachment of the compensation element 500. Plug-in, latching, clamping and/or snap-fit connections should be mentioned by way of example.

Figure 8:
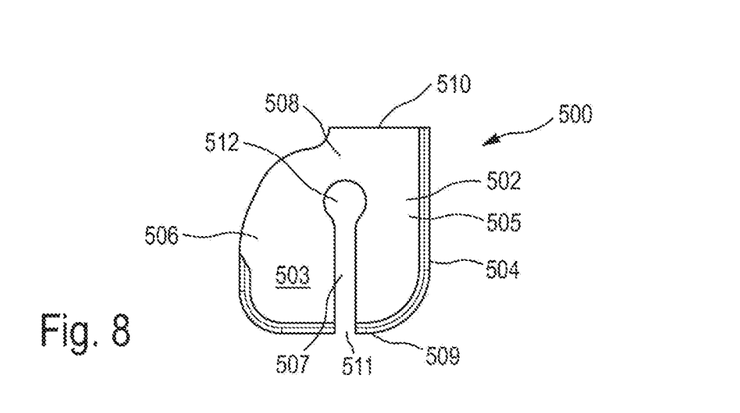

In the embodiment shown, the compensation element 500 can be plugged onto the reference foot 400 in a force-fitting and/or form-fitting manner. For this purpose, the compensation element 500 has a receiving pocket 503 on an element underside 502 lying posteriorally opposite the element upper face 501 (see FIG. 8). The receiving pocket 503 is dimensionally matched to the dimensions of the medial reference foot 400. The medial reference foot 400 can be received in the receiving pocket 503 in a force-fitting and/or form-fitting manner.

In the attached state, the element upper face 501 covers the medial foot upper face 401. Owing to the present thickness t1, the element upper face 501 is accordingly arranged spaced apart anteriorally—with respect to the plane of the drawing of FIG. 1—above the medial foot upper face 401.

In the embodiment shown the compensation element 500 also has an outer rim 504. The outer rim 504 protrudes from the element underside 502 in the normal direction thereof. With respect to the configuration shown in FIGS. 1 to 4, the outer rim 504 protrudes posteriorly from the element underside 502. The outer rim 504 is connectable in a form-fitting manner to an outer circumference (without reference sign) of the medial reference foot 400. For this purpose, the outer rim 504 is shaped in a complementary manner to the aforementioned outer circumference, and vice versa. The outer rim 504 engages around the outer circumference of the reference foot 400, and therefore the compensation element 500 is attached to the reference foot 400 in the manner of a lid.

In the embodiment shown, the outer rim 504 forms an outer boundary of the receiving pocket 503.

In the embodiment shown, the receiving pocket 503 is firstly open posteriorally. Secondly, the receiving pocket 503 is open in the distal direction—at any rate with respect to the configuration shown in FIGS. 1 to 4. By this means, the compensation element 500 can be pushed distally onto the reference foot 400. Alternatively, the compensation element 500 can be plugged on posteriorally. The outer rim 504 delimits the receiving pocket 503 here mediolaterally and proximally.

In addition, the compensation element 500 which is shown in detail in FIGS. 5 to 8 has a lateral element section 505, a medial element section 506, a separating gap 507 and a joint section 508.

Figure 1:
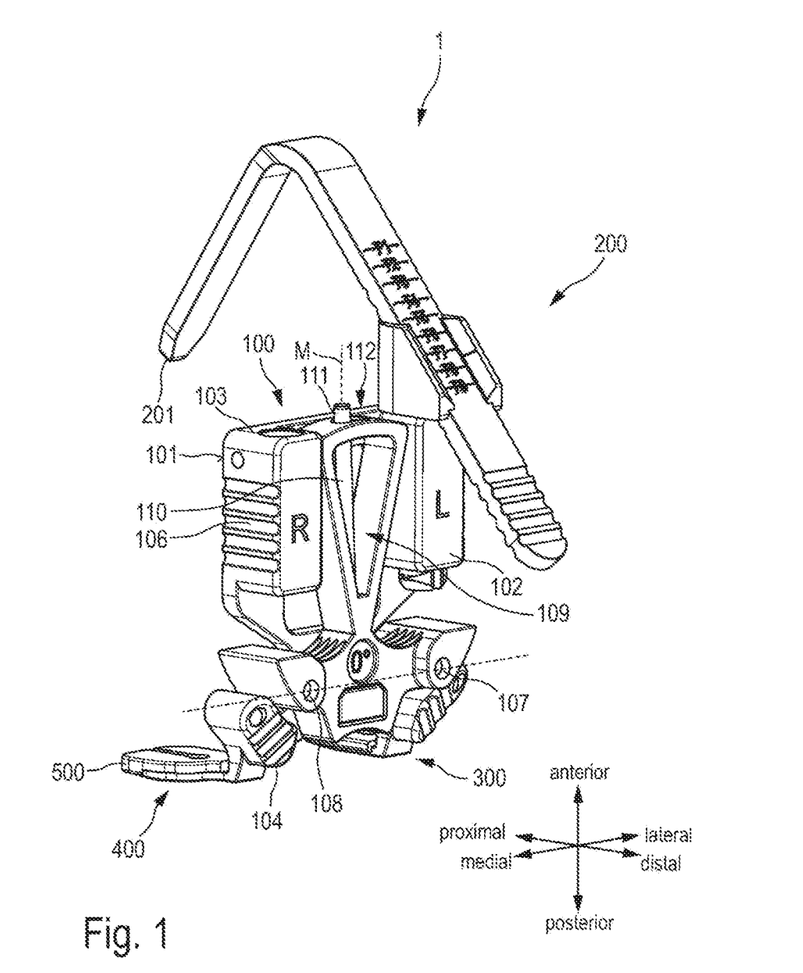
FIG. 1 shows a schematic perspective view of an embodiment of a surgical instrument according to the disclosure.
Figure 2:
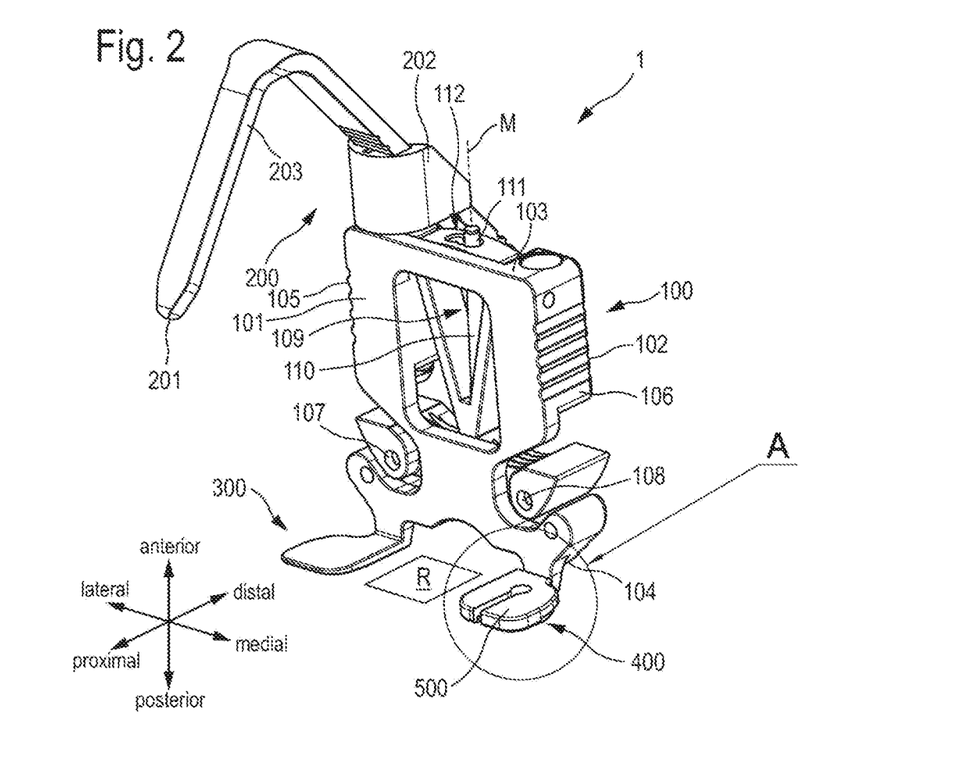
FIG. 2 shows a further schematic perspective view of the surgical instrument according to FIG. 1.
Figure 3:
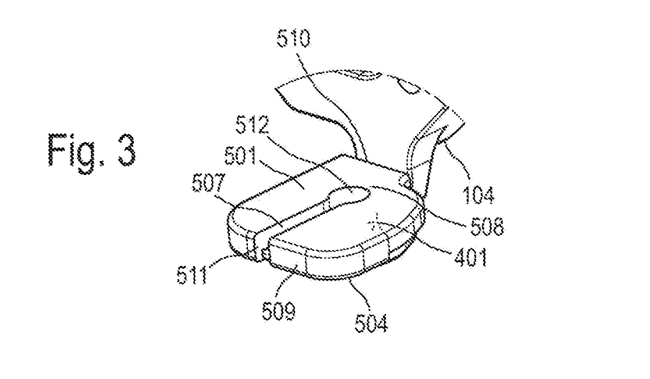
FIG. 3 shows an enlarged detailed view of the surgical instrument in a region of detail A according to FIG. 2.

The separating gap 507 separates the two element sections 505, 506 from each other and is elongate here parallel to the proximodistal axis indicated in FIGS. 1 and 2. The separating gap 507 is open at one end. In the present case, the separating gap extends from an element rear face 509 into the compensation element 500. Starting from its open end, the separating gap 507 is elongate in the direction of an element front face 510. The element front face 510 lies distally opposite the element rear face 509. In the present case, the separating gap 507 has, facing away from its opening 511, an expanded portion 512.

The joint section 508 is arranged at that end of the separating gap 507 which faces away from the opening 511 and connects the two element sections 505, 506 to one another in an elastically movable-joint manner. The joint section 508 permits a limited elastic springing up of the compensation element 500 with respect to the mediolateral axis (see in particular FIGS. 3 and 4). By this means, the two element sections 505, 506 are elastically spread open in relation to one another when the compensation element 500 is plugged onto the medial reference foot 400. The outer rim 504 then bears in an elastically prestressed manner against the outer circumference of the reference foot 400. The elastic prestress counteracts an inadvertent detaching of the compensation element 500. The joint section 508 here forms a type of solid body joint with an anteroposteriorally oriented joint axis.

In the embodiment shown, the compensation element 500 is produced from a plastic which is suitable for medical use. Such plastics are known to a person skilled in the art. Alternatively, the compensation element can be manufactured from metal.

Figure 9:
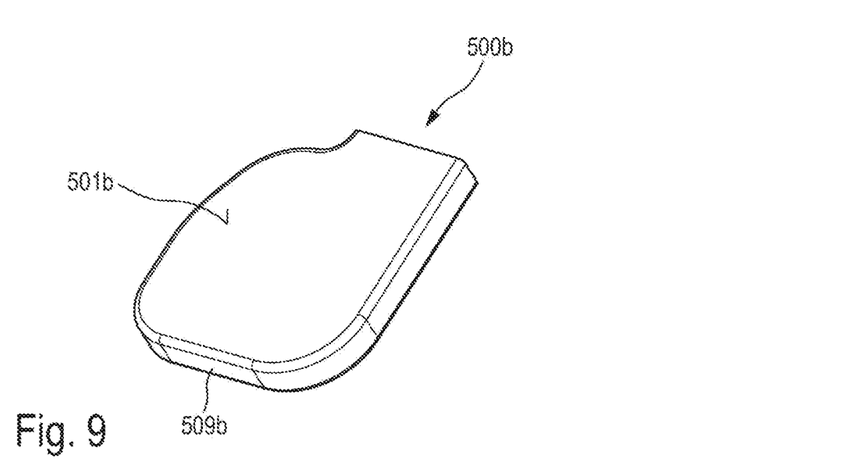
FIGS. 9 and 10 show different schematic perspective views of a variant of the compensation element according to FIGS. 6 to 8.
Figure 10:
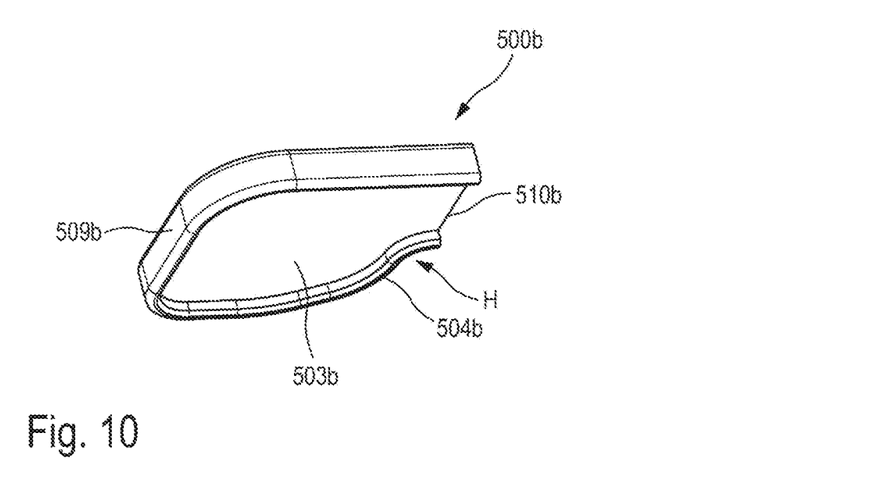

FIGS. 9 and 10 show a compensation element 500b. The compensation element 500b is a variant of the compensation element 500 according to FIGS. 6 to 8. To avoid repetitions, only substantial differences of the compensation element 500b in comparison to the compensation element 500 will be explained below. Identical features will not be discussed once again. Instead, reference is expressly made to the description in conjunction with FIGS. 6 to 8.

In contrast to the compensation element 500, the compensation element 500b does not have a separating gap. In addition, the compensation element 500b does not permit plugging on in the distal direction. Instead, the compensation element 500b can only be plugged on posteriorally. To this extent, there is in turn a receiving pocket 503b. The latter is bordered by an outer rim 504b. The outer rim 504b here is elastically flexible. The elastic flexibility of the outer rim 504b can be brought about by material and/or design. In the present case, firstly the selection of material and secondly the comparatively thin configuration of the outer rim 504b contributes to the elastic flexibility thereof. The effect achieved by the elastic flexibility of the outer rim 504b is improved clamping on the relevant reference foot. The outer rim 504b here has an undercut H (see FIG. 10). The undercut H prevents the compensation element 500b from being able to be plugged distally onto the relevant reference foot. At the same time, proximal pulling off of the compensation element 500b is opposed.

Furthermore with respect to FIGS. 1 to 5, the surgical instrument 1 here has, in the region of its reference block 100, an aperture 109 and an alignment element 110 arranged in the aperture 109.

The aperture 109 extends proximodistally right through between the block rear face 101 and the block front face 102 and forms a viewing opening through which the surgeon can look in the proximal viewing direction at the distal end face S. The aperture 109 is shaped approximately triangularly here. Alternative shapes are of course conceivable.

The alignment element 110 is elongate anteroposteriorly and arranged approximately centrally in the aperture 109 with respect to the mediolateral axis. The alignment element 110 serves for aligning the surgical instrument 1 along what is referred to as the Whiteside's line W (see FIG. 5). The Whiteside's line W, in the same manner as the posterior condyle line P, forms an anatomical landmark for aligning the surgical instrument 1 on the femur F. Using the alignment element 110, the surgeon can align the surgical instrument 1 with respect to the Whiteside's line W in the intraoperative situation shown with reference to FIG. 4. For this purpose, the alignment element 110 is brought—with respect to a posteriorally directed viewing direction—into overlap with the Whiteside's line W.

The alignment element 110 is elongate along its longitudinal axis M between a posterior end, not shown specifically in the figures, and an anterior end 111. The two ends can also be referred to as first end and second end 111. The second end 111 protrudes anteriorly beyond the block upper face 103. The first end is mounted in a manner not shown specifically on the reference block 100 so as to be movable about a proximodistally oriented pivot axis (no reference sign). By this means, the alignment element 110 can be moved by manipulation at the second end 111 between different positions.

In the present case, movement between a first position shown in the figures and a second position, not shown specifically, is possible. In the first position, the longitudinal axis M is inclined by 3° in relation to the normal direction of the reference plane R (see FIG. 2). In the second position, the inclination is 5°. The second end 111 is held movably between the two positions in a receiving cut-out 112 of the reference block 100 (see FIG. 2). The receiving cut-out is shaped here in the form of an elongate hole. In both positions of the alignment element 110, the second end 111 is held either at the one or the other end of the elongate hole or of the receiving cut-out 112.

The movability of the alignment element 110 permits an adapted setting of the UE rotation. In the present case, an UE rotation of 3° can be set in the first position of the alignment element 110. In the second position, there is an UE rotation of 5°.

The invention claimed is:

1. A surgical instrument for use in a knee joint replacement operation, the surgical instrument comprising:
   a reference block with a block rear face that is proximally oriented, the reference block configured to bear on a distal end face of a resected femur;
   a stylus arranged on a block upper face of the reference block, the stylus having a stylus tip that protrudes proximally beyond the block rear face and is configured to bear on an anterior face of the femur;

two reference feet that are spaced apart mediolaterally from one another and are each arranged on the reference block in a region of an underside of the reference block lying posteriorly opposite the block upper face, each of the reference feet having a foot upper face that is anteriorly oriented and protruding proximally beyond the block rear face, wherein the foot upper faces are arranged in a common reference plane and are each configured to bear on a posterior condyle of the femur;

at least two reference bores that each extend orthogonally to the block rear face continuously from the block rear face as far as a block front face distally opposite the block rear face and are each configured for receiving a reference pin which is introducible into the distal end face of the femur, wherein the at least two reference bores are spaced apart from one another along a virtual spacing line which is elongate mediolaterally and parallel to the common reference plane; and at least one compensation element configured for form-fitting and/or force-fitting releasable connection to one of the two reference feet, the at least one compensation element having an anteriorly oriented element upper face configured to bear against a patient's posterior condyle.

2. The surgical instrument according to claim 1, wherein the at least one compensation element has an underside and a receiving pocket on the underside, the receiving pocket being sunk anteriorally and open posteriorally, the reference foot being receivable in the receiving pocket in a form-fitting manner.

3. The surgical instrument according to claim 1, wherein the at least one compensation element has an underside and an outer rim on the underside, the outer rim protruding posteriorally and being connectable in a form-fitting manner to an outer circumference of said one of the two reference feet.

4. The surgical instrument according to claim 3, wherein the outer rim is elastically flexible.

5. The surgical instrument according to claim 1, wherein the at least one compensation element comprises:
   a lateral element section;
   a medial element section;
   a separating gap that separates the lateral element section and the medial element section from one another, the separating gap having a first end and a second end, the separating gap being elongate proximodistally and open at the first end; and
   a joint section arranged at the second end of the separating gap, the joint section connecting the lateral element section and the medial element section to one another in an elastically movable-joint manner.

6. The surgical instrument according to claim 1, wherein the at least one compensation element comprises a plurality of compensation elements that differ with respect to anteroposterior thickness.

7. The surgical instrument according to claim 6, wherein the plurality of compensation elements comprises three compensation elements having anteroposterior thicknesses of 1 mm, 2 mm and 3 mm.

8. The surgical instrument according to claim 1, wherein the reference block has an aperture reaching between the block rear face and the block front face, and an alignment element which is arranged in the aperture, is elongate substantially in an anteroposterior direction and is configured for alignment along a Whiteside's line of the femur.

9. The surgical instrument according to claim 8, wherein the alignment element is movable relative to the reference block between a first position, in which the alignment element is oriented at a first angle with respect to the virtual spacing line of the reference bores, and a second position, in which the alignment element is oriented at a second angle with respect to the virtual spacing line of the reference bores.

10. The surgical instrument according to claim 9, wherein the alignment element has a posterior end, which is mounted on the reference block so as to be movable about a proximodistally oriented pivot axis, and an anterior end, which protrudes beyond the block upper face and is configured for manual movement of the alignment element between the first position and the second position.

* * * * *